United States Patent
Zapala

(10) Patent No.: US 9,332,904 B2
(45) Date of Patent: May 10, 2016

(54) QUANTIFYING OCULAR COUNTER ROLL

(75) Inventor: David A. Zapala, Ponte Vedra Beach, FL (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 352 days.

(21) Appl. No.: 14/122,599

(22) PCT Filed: May 30, 2012

(86) PCT No.: PCT/US2012/040009
§ 371 (c)(1),
(2), (4) Date: Dec. 27, 2013

(87) PCT Pub. No.: WO2012/166803
PCT Pub. Date: Dec. 6, 2012

(65) Prior Publication Data
US 2014/0104575 A1    Apr. 17, 2014

Related U.S. Application Data

(60) Provisional application No. 61/491,764, filed on May 31, 2011.

(51) Int. Cl.
| | | |
|---|---|---|
| A61B 3/14 | (2006.01) |
| A61B 3/113 | (2006.01) |
| A61B 5/12 | (2006.01) |
| A61B 5/11 | (2006.01) |
| A61B 5/00 | (2006.01) |

(52) U.S. Cl.
CPC ............... *A61B 3/113* (2013.01); *A61B 5/1121* (2013.01); *A61B 5/12* (2013.01); *A61B 5/4863* (2013.01); *A61B 2562/0219* (2013.01)

(58) Field of Classification Search
CPC ........ A61B 3/113; A61B 3/0025; A61B 3/00; A61B 2562/0219; A61B 5/1121; A61B 5/4023; A61F 2009/00846
USPC ............. 351/200–247; 359/24, 630; 396/147, 396/287, 378
See application file for complete search history.

(56) References Cited

U.S. PATENT DOCUMENTS

| | | |
|---|---|---|
| 2007/0161875 A1 | 7/2007 | Epley |
| 2010/0036289 A1 | 2/2010 | White et al. |

FOREIGN PATENT DOCUMENTS

| | | |
|---|---|---|
| WO | WO 2007/107975 | 9/2007 |
| WO | WO 2010/117386 | 10/2010 |

OTHER PUBLICATIONS

International Search Report and Written Opinion in International Application No. PCT/US2012/040009, mailed Dec. 12, 2012, 11 pages.
International Preliminary Report on Patentability in International Application No. PCT/US2012/040009, mailed Dec. 12, 2013, 8 pages.
Ramey et al., "A novel haploscopic viewing apparatus with a three-axis eye tracker," *J of AAPOS*, Oct. 2008, 12(5):498-503.
Vieville and Masse, "Ocular Counter-rolling during Active Head Tilting in Humans," *Acta Otolaryngol (Stockh)*, 1987, 103:280-290.

*Primary Examiner* — Mahidere Sahle
(74) *Attorney, Agent, or Firm* — Fish & Richardson P.C.

(57) ABSTRACT

This document provides methods and materials for quantifying ocular counter roll and detecting vestibular otolith damage. For example, devices for quantifying ocular counter roll, methods of making devices for quantifying ocular counter roll, and methods for using a device to quantify (e.g., quantify indirectly) ocular counter roll are provided.

20 Claims, 11 Drawing Sheets

QUANTIFYING OCULAR COUNTER ROLL

CROSS-REFERENCE TO RELATED APPLICATIONS

This application is a National Stage application under 35 U.S.C. 371 of International Application No. PCT/US2012/040009, having an International Filing Date of May 30, 2012, which claims the benefit of U.S. Provisional Application Ser. No. 61/491,764, filed May 31, 2011. The disclosure of the prior application is considered part of (and is incorporated by reference in) the disclosure of this application.

BACKGROUND

1. Technical Field

This document relates to methods and materials for quantifying ocular counter roll (OCR) and detecting vestibular otolith damage. For example, this document relates to devices for quantifying OCR, methods of making devices for quantifying OCR, and methods for using a device to quantify (e.g., quantify indirectly) OCR.

2. Background Information

The otolith organs (the utricle and saccule) of the inner ear vestibular system are the primary gravity sensors of the body. Activation of the otolith organs by linear acceleration generates spinal and ocular reflexes that act to maintain posture and gaze. OCR is an example of an otolith-ocular reflex in response to otolith activation. When the head is tilted to the side (ear moved toward the shoulder), the eyes roll in the opposite direction. This head tilt induced OCR is an orienting reflex that tends to align the eyes with the horizon. Damage to the otolith organs or their central connections can impair body and ocular stabilization. This can cause complaints of dizziness or imbalance that are difficult to diagnose without sophisticated and expensive measurement equipment. As a consequence, the cause of these disorders is often missed.

SUMMARY

This document provides methods and materials for quantifying OCR and detecting vestibular otolith damage. For example, this document provides devices for quantifying OCR, methods of making devices for quantifying OCR, and methods for using a device provided herein to quantify (e.g., quantify indirectly) OCR. As described herein, a device can be designed such that health care providers can quantitate OCR behavior to detect patients with a deficit in OCR. A deficit in OCR can indicate the presence of otolith reflex damage.

OCR is typically measured directly by tests such as unilateral centrifugation with torsional eye movement recording. The equipment required can be expensive, and using video to measure torsional eye movements that underlie the OCR response can be technically challenging. The methods and materials provided herein can be used to quantify OCR indirectly. Such methods and materials can be used in a patient exam room and can allow health care providers to use standard measurement techniques without the use of complicated or expensive equipment to identify patients with otolith mediated causes of dizziness and imbalance that might otherwise go undiagnosed.

In some cases, a device provided herein can include a viewing tube, an eye piece component, and an inclinometer. An inclinometer can be coupled to the eye piece component at or near the proximal end of a viewing tube to measure the degree of eye piece tilt relative to gravitational zero. A viewing tube can include a straight edge internal calibration line visible inside the viewing tube that can be used to align a device provided herein to an external target line. Such an external target line can be a straight line projected onto a screen or wall. When the external target line is tilted and the subject is instructed to tilt their head to match the perceived target line tilt while looking through the device provided herein, the angle of head tilt will be different from (typically greater than) the angle of target line tilt due to OCR. This difference is proportional to the amount of induced OCR.

Using the inclinometer to measure the amount of head tilt required to match perceptually the tilt of the target line, OCR can be calculated as the difference between head tilt and target line tilt. This simple method indirectly measures the OCR without the use of complicated or expensive equipment. Subjects with utricular deficits can display little or no OCR behavior as compared to control subjects known not to have utricular deficits. This can allow health care providers to detect otolith damage readily in patients with symptoms of dizziness or imbalance, and can allow patients to be properly diagnosed and treated.

In general, one aspect of this document features a device for quantifying ocular counter roll. The device comprises, or consists essentially of, (a) a viewing tube configured to have a hollow inner lumen; (b) a calibration line configured to be fixed with respect to the viewing tube; (c) an eye piece component configured to have a hollow inner lumen wherein the eye piece component allows a clear viewing path through the viewing tube; and (d) an inclinometer. The device can be mechanically fixed to viewing goggles, glasses, or a handle. The device can be mechanically fixed to the lens of a pair of goggles or glasses. The device can be mechanically fixed to a handle. The eye piece component can be configured to fit over an end of the viewing tube. The viewing tube can be configured to fit over an end of the eye piece component. The device can comprise two inclinometers.

In another aspect, this document features a method for quantifying ocular counter roll using a device comprising a viewing tube, a calibration line configured to be fixed with respect to the viewing tube, an eye piece component configured to allow a clear viewing path through the viewing tube, and an inclinometer to view an external target line placed within about 1 to 6 meters of the subject. The method comprises, or consists essentially of, (a) taking a baseline measurement from the inclinometer when a subject perceives the calibration line and the external target line are parallel; (b) adjusting the angle of the external target line by 20° or less; (c) measuring the angle of the subject's head tilt with the inclinometer when the subject perceives the calibration line and the external target line are parallel; and (d) quantifying ocular counter roll as the difference between the angle of the external target line and the measured angle of the subject's head tilt. The device can be mechanically fixed to viewing goggles, glasses, or a handle. The device can be mechanically fixed to the lens of a pair of goggles or glasses. The device can be mechanically fixed to a handle. The eye piece component can be configured to fit over an end of the viewing tube. The viewing tube can be configured to fit over an end of the eye piece component. The device can comprise two inclinometers.

In another aspect, this document features a method for quantifying ocular counter roll using a device comprising a viewing tube, a calibration line configured to be fixed with respect to the viewing tube, an eye piece component configured to allow a clear viewing path through the viewing tube, and an inclinometer to view an external target line placed within about 1 to 6 meters of the subject. The method comprises, or consists essentially of, (a) a human subject looking through the eye piece component and the viewing tube to visualize the calibration line and the external target line; (b) the subject, optionally, calibrating the device by manually rotating the viewing tube about the viewing axis until the calibration line and the external target line are parallel; (c) the subject tilting their head with the device held fixed in relation to the subject's head until the subject perceives the calibration line and the external target line are parallel after the angle of the external target line is tilted by 20° or less; and (d) quantifying ocular counter roll as the difference between the subject's head tilt and external target line tilt. The subject's vision from the opposite eye can be precluded. The device can be mechanically fixed to viewing goggles, glasses, or a handle. The device can be mechanically fixed to the lens of a pair of goggles or glasses. The device can be mechanically fixed to a handle. The eye piece component can be configured to fit over an end of the viewing tube. The viewing tube can be configured to fit over an end of the eye piece component. The device can comprise two inclinometers.

In another aspect, this document features a method for quantifying ocular counter roll using a device comprising a viewing tube, a calibration line configured to be fixed with respect to the viewing tube, an eye piece component configured to allow a clear viewing path through the viewing tube, and an inclinometer to view an external target line placed within about 1 to 6 meters of the subject. The method comprises, or consists essentially of, (a) taking a baseline measurement from the inclinometer attached to the eyepiece component when a subject perceives the calibration line and the external target line are parallel; (b) adjusting the angle of the external target line by 20° or less; (c) manually tilting the subject's head to the same angle as the external target line with the device held fixed in relation to the subject's head, measuring head tilt angle with the inclinometer attached to the eye piece; (d) measuring the angle of the subject's head tilt adjustment with the inclinometer attached to the viewing tube after the subject perceives the calibration line and the external target line are parallel; and (e) quantifying ocular counter roll as the amount of the subject's head tilt adjustment. The device can be mechanically fixed to viewing goggles, glasses, or a handle. The device can be mechanically fixed to the lens of a pair of goggles or glasses. The device can be mechanically fixed to a handle. The eye piece component can be configured to fit over an end of the viewing tube. The viewing tube can be configured to fit over an end of the eye piece component. The device can comprise two inclinometers.

In another aspect, this document features a method for quantifying ocular counter roll using a device comprising a viewing tube, a calibration line configured to be fixed with respect to the viewing tube, an eye piece component configured to allow a clear viewing path through the viewing tube, and an inclinometer to view an external target line placed within about 1 to 6 meters of the subject. The method comprises, or consists essentially of, (a) a human subject looking through the eye piece component and the viewing tube to visualize the calibration line and the external target line; (b) the subject calibrating the viewing tube, if needed, by manually rotating the viewing tube about the viewing axis while fixing the eye piece component relative to the viewer's head until the calibration line and the external target line are parallel; (c) the subject allowing their head to be adjusted to the same angle of 20° or less as the external target line with the device held fixed in relation to the subject's head; (d) the subject adjusting their head tilt angle with the viewing tube held fixed in relation to the subject's head until the subject perceives the calibration line and the external target line are parallel; and (e) quantifying ocular counter roll as the amount of the subject's head tilt adjustment. The subject's vision from the opposite eye can be precluded. The device can be mechanically fixed to viewing goggles, glasses, or a handle. The device can be mechanically fixed to the lens of a pair of goggles or glasses. The device can be mechanically fixed to a handle. The eye piece component can be configured to fit over an end of the viewing tube. The viewing tube can be configured to fit over an end of the eye piece component. The device can comprise two inclinometers.

In another aspect, this document features a method for determining if a human subject has otolith damage. The comprises, or consists essentially of, quantifying ocular counter roll of the subject as described herein, comparing the ocular counter roll of the subject to ocular counter roll measurements of control subjects known not to have otolith damage, and diagnosing otolith damage if the ocular counter roll of the subject is smaller than or larger than a counter roll of control subjects known not to have otolith damage.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

This document provides methods and materials for quantifying OCR. For example, this document provides devices for quantifying OCR, methods of making devices for quantifying OCR, and methods for using a device provided herein to quantify (e.g., quantify indirectly) OCR.

A device provided herein can include a viewing tube, an eye piece component, and an inclinometer. The eye piece component can be configured to be integral with, to be attach to, or to fit over the proximal end of the viewing tube or a position near the proximal end of the viewing tube. The inclinometer can be configured to be integral with, to be attached to, or to fit over a portion of the eye piece or viewing tube. A viewing tube can include a calibration line visible inside the viewing tube that can be used to align the viewing tube to an external target line. Such an external target line can be a vertical or horizontal line projected onto a screen or wall.

Figure 1:
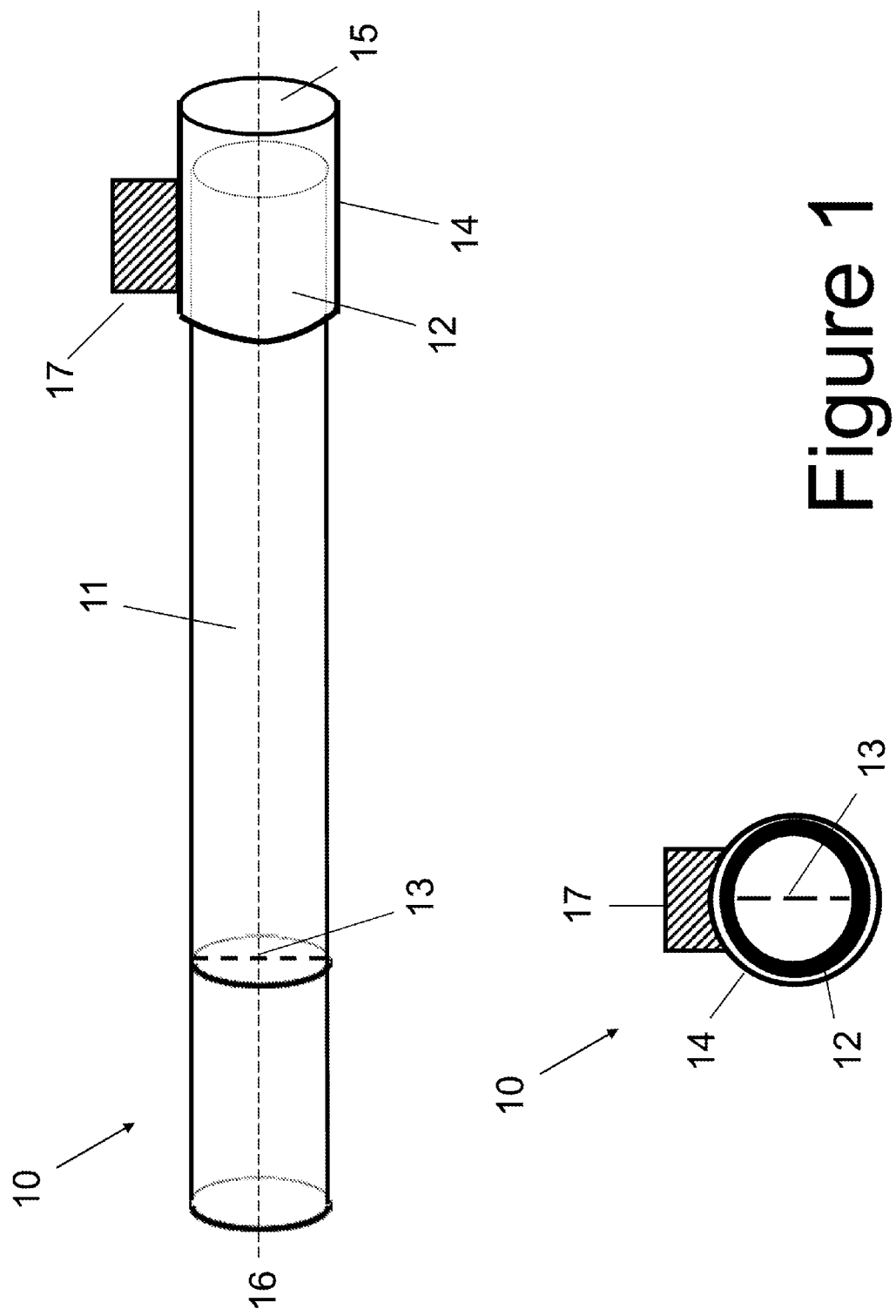
FIG. 1 contains a side view and a front view of one example of a device for quantifying OCR.

A device for quantifying OCR as described herein can be used to provide a psychophysical method to quantify OCR. The term "psychophysical" as used herein refers to a general class of methods that can be applied to study a perceptual system. With reference to FIG. 1, a subject can look through an eye piece component 14 and align a calibration line 13 inside a viewing tube 11 such that it is parallel with a projected external target line. Once viewing tube 11 is calibrated, the external target line can be tilted by 20° or less. A subject can then be asked to tilt their head to match the perceived angle of the external target line, such that device 10 moves as one unit with the subject's head. The degree of head tilt can then be measured with an inclinometer 17. When a visual target is tilted and the subject is asked to tilt their head to match the perceived external target line angel, the amount of head tilt and the amount of target tilt will not be equal. This difference is proportional to the amount of induced OCR. The indirect measurement of OCR can indicate if a subject has damage to the otolith organs of the inner ear vestibular system. A subject with otolith damage will display an OCR that is less than expected as compared to the OCR of control subjects known not to have otolith damage.

In some cases, a device to quantify OCR provided herein can be mechanically fixed. For example, with reference to FIG. 1, eye piece component 14 can be mounted on a lens of a set of viewing goggles. The goggle lens without mounted device 10 can be covered to preclude extraneous visual cues. When the set of viewing goggles with mounted device 10 is worn, device 10 is fixed in place relative to the subject's head. Device 10 moves with the head when the subject is instructed to tilt their head to match the perceived external line tilt. In some cases, a device to quantify OCR 10 can be mounted on a handle. For example, viewing tube 11 or eye piece component 14 can be mounted anywhere along their lengths on a handle of any appropriate length at any appropriate angle such that a subject can comfortably grasp the handle and bring device 10 up to the eye.

With reference to FIG. 1, viewing tube 11 of device 10 can be any appropriate shape configured to have a hollow inner lumen. The inner lumen can provide a clear view of calibration line 13 and an external target line when a subject looks through eye piece component 14 attached at or near proximal end 12 of viewing tube 11. In some cases, the inner lumen of viewing tube 11 can be illuminated to make visibility of calibration line 13 clear.

A viewing tube of a device provided herein can be composed of any appropriate material. For example, a viewing tube of a device provided herein can be composed of translucent material such that some light is allowed to pass through the walls of the viewing tube into the hollow lumen and the vision of a subject looking through the viewing tube is obstructed except through the open distal end of the viewing tube. Examples of translucent materials that can be used to make a viewing tube provided herein include, without limitation, acrylic (plexiglass), polycarbonate, polyvinyl, flouroelastomers, and acrylates. In some cases, a viewing tube of a device provided herein can be composed of opaque material such that no light is allowed to pass through the walls of the viewing tube into the hollow lumen and the vision of a subject looking through the viewing tube is completely occluded except through the open distal end of the viewing tube, where light is allowed to enter the hollow lumen. Examples of opaque materials that can be used to make a viewing tube provided herein include, without limitation, steel, brass, nickel, copper, aluminum, polystyrene, polyaryletheretherketone, polyphenylene sulphide, and polypropylene.

A viewing tube of a device provided herein can be designed to have dimensions appropriate for a subject to have unobstructed view of a calibration line inside the viewing tube and an external target line. For example, a viewing tube can be between 2 cm and 5 cm in diameter to encompass fully a subject's eye and 5 cm and 50 cm in length. Pediatric viewing tubes can be designed using smaller dimensions. For example, a pediatric viewing tube can be between 1.5 cm and 4.5 cm in diameter and 5 cm and 50 cm in length.

A calibration line of a device provided herein can have any appropriate configuration that allows the calibration line to be visible to the test subject. In some cases, the calibration line can be located within a viewing tube. In some cases, the calibration line can be located outside the viewing tube provided that it is visible to the test subject during use and provided that it is fixedly attached to the device such that it rotates as the user rotates the device.

Figure 2:
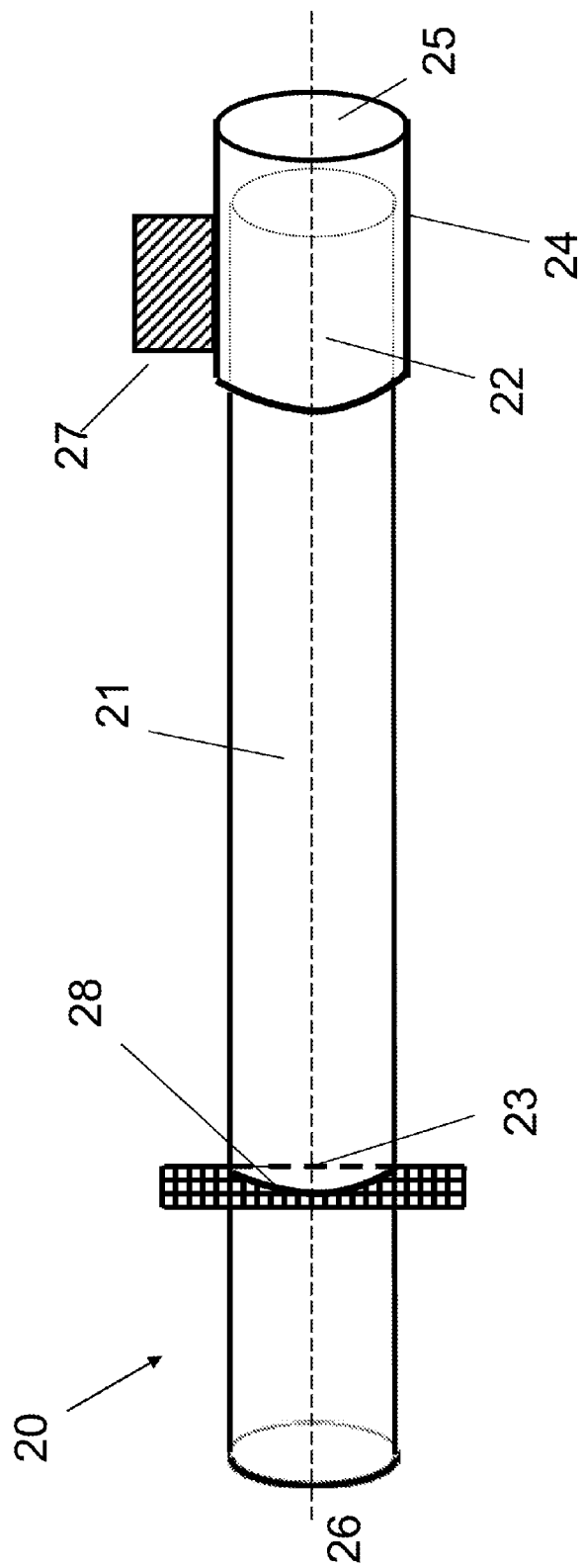
FIG. 2 is a side view of an exemplary device for quantifying OCR.

With reference to FIG. 1, calibration line 13 of device 10 can be a straight edge on a shape configured to fit inside viewing tube 11. The shape containing the straight edge calibration line can be secured in place inside the viewing tube with materials such as, without limitation, glue, rubber cement, epoxy, and thermoplastics. With reference to FIG. 2, a device 20 configured to allow for the quantification of OCR can include a calibration line 23. Calibration line 23 can be a straight edge of an object or shape inserted into a slit 28 cut into a viewing tube 21. The object or shape inserted into slit 28 can be secured in place with materials such as, without limitation, glue, rubber cement, epoxy, thermoplastics, and adhesive tapes.

A calibration line of a device provided herein can be composed of any appropriate material. For example, a viewing tube of a device provided herein can be composed of material such that the calibration line is a straight edge and the calibration line can be easily visualized by a subject while looking through the viewing tube. Examples of materials that can be used to make a calibration line provided herein include, without limitation, steel, brass, nickel, copper, aluminum, polystyrene, polyaryletheretherketone, polyphenylene sulphide, and polypropylene. In some cases, a straight edge of a measurement device can be used to make a calibration line provided herein.

A calibration line of a device provided herein can be designed to have dimensions appropriate to be attached to the device. In some cases, a calibration line can be designed to have dimensions appropriate for it to be contained within a viewing tube and to provide a straight edge within the viewing tube. For example, a calibration line can be a straight edge on a shape configured to fit inside a viewing tube. The dimensions of the shape containing a straight edge calibration line can be essentially those of a viewing tube or less so as to fit inside the viewing tube. In some cases, a calibration line can be a straight edge on an object of an appropriate width to fit tightly into a slit cut into a side of a viewing tube. The position of a calibration line inside a viewing tube can be such that the calibration line appears as a crisp image to the subject. A calibration line can be positioned between 4 cm and 50 cm from the subject's eye at the proximal end of the eye piece component.

With further reference to FIG. 1, eye piece component 14 of device 10 can be any appropriate shape configured to fit over proximal end 12 of viewing tube 11. Proximal end 12 of viewing tube 11 can fit into eye piece component 14 such that viewing tube 11 can be rotated about viewing axis 16. Proximal end 15 of eye piece component 14 can be open to provide a clear view through viewing tube 11 when device 10 is brought to the eye.

An eye piece component of a device provided herein can be composed of any appropriate material. For example, an eye piece component of a device provided herein can be composed of material such that the viewing tube can rotate with the applied force of the human hand within the eye piece component. Examples of materials that can be used to make an eye piece component provided herein include, without limitation, acrylic (plexiglass), polycarbonate, polyvinyl, flouroelastomers, acrylates, polystyrene, polyaryletheretherketone, polyphenylene sulphide, polypropylene, steel, brass, nickel, copper, and aluminum.

An eye piece component of a device provided herein can be designed to have dimensions appropriate to fit over the proximal end of a viewing tube. The diameter of an eye piece component can be just slightly greater or slightly smaller than the diameter of a viewing tube so as to allow the viewing tube to rotate about the viewing axis when turned by the subject while the proximal end of the viewing tube remains within the eye piece component. The fit between the eye piece component and the proximal end of the viewing tube can be tight enough to prevent the eye piece component from slipping off the viewing tube and loose enough to allow the viewing tube to rotate within the eye piece component. An eye piece component can be between 1.5 cm and 5.5 cm in length. In some cases, the eye piece component and the viewing tube can have threads. For example, the outside surface of the proximal end of the viewing tube can have threads that interlock with threads on the inside surface of the eye piece component. The eye piece component can screw onto the proximal end of the viewing tube so as not to slip off while allowing the viewing tube to turn within the eye piece component.

An inclinometer of a device provided herein can be any appropriate type of inclinometer that provides the measurement of head tilt. In some cases, an inclinometer of a device provided herein can be an inclinometer that provides the measurement of rotation on the viewing tube about the viewing axis. Examples of types of inclinometers that can be used include, without limitation, ball inclinometers, bubble inclinometers, capacitive tilt sensors, electrolytic tilt sensors, micro machined silicon tilt sensor inclinometer IC's, high precision closed loop servo inclinometer sensors, inclinometers with a built in digital display and output, inclinometer sensors with a remote digital display, absolute encoder inclinometers, and custom designed inclinometers. In some cases, a smart phone can be used as an inclinometer by attaching the smart phone to a device provided and using a spirit level application for measuring tilt.

Figure 3:
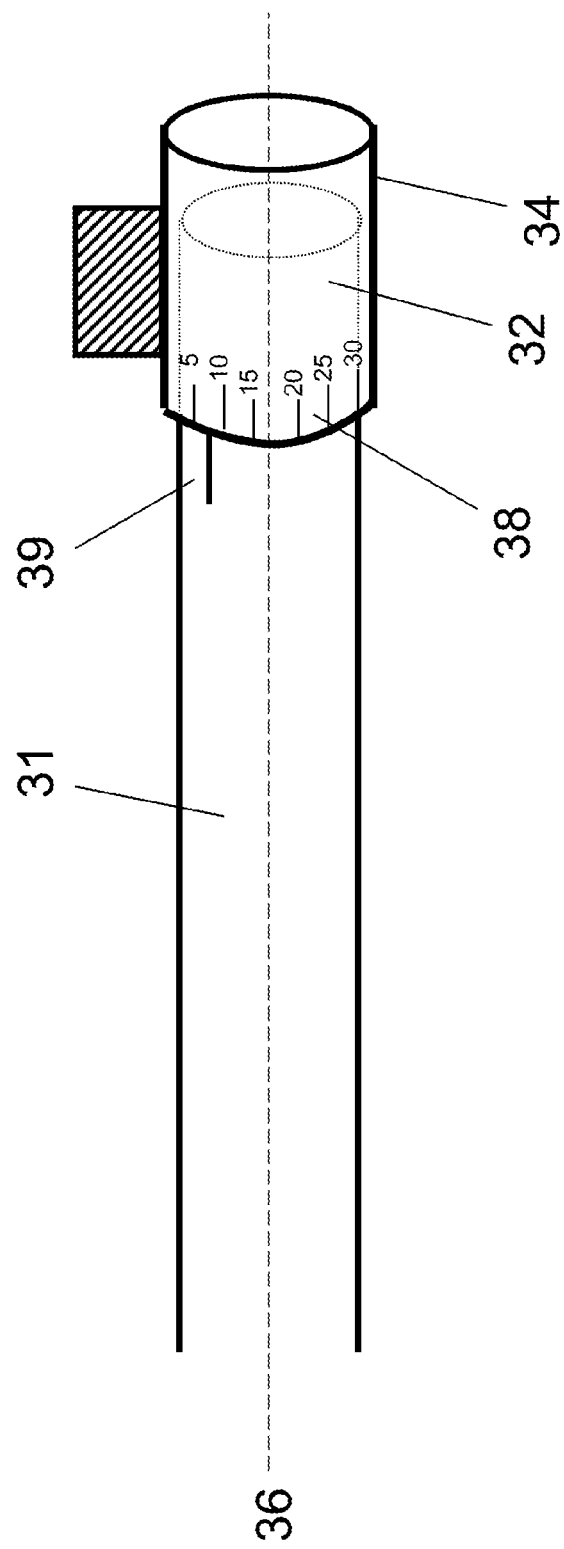
FIG. 3 is a side view of an exemplary device for quantifying OCR.

In some cases, a device provided herein can have markings at the distal end of an eye piece component. For example, with reference to FIG. 3, marks indicating increments of degrees 38 can be made on the distal end of eye piece component 34. A mark 39 can be made on the viewing tube so as to line up with marks indicating increments of degrees 38 on eye piece component 34. Changes in viewing tube 31 angle relative to eye piece component 34 can be measured when viewing tube 31 is manually rotated about viewing axis 36.

Figure 4:
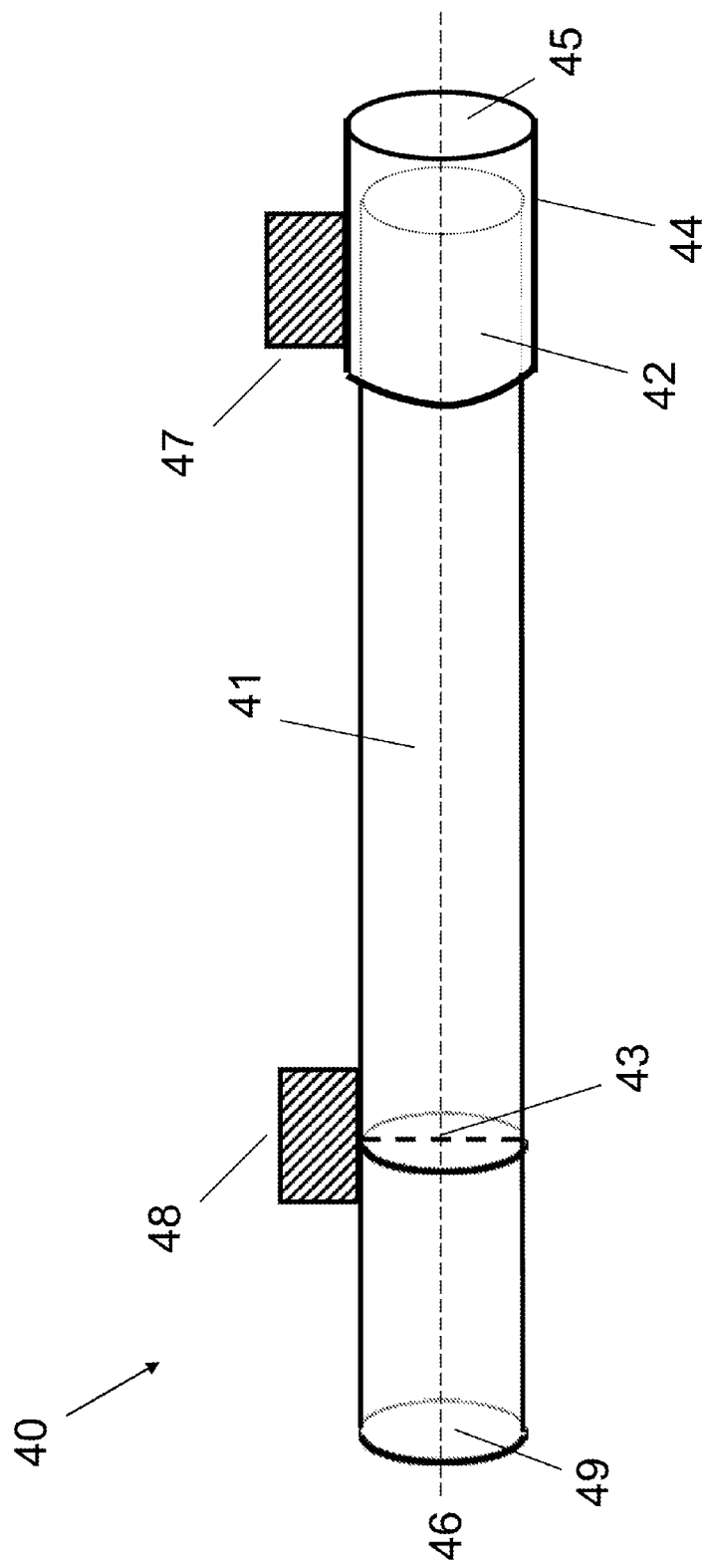
FIG. 4 is a side view of an exemplary device for quantifying OCR.

In some cases, a device provided herein can include two or more inclinometers. For example, with reference to FIG. 4, a device to quantify OCR 40 can include an inclinometer 47. Inclinometer 47 can be coupled to an eye piece component 44 at a proximal end 42 of a viewing tube 41. Inclinometer 47 can be used to measure the number of degrees eye piece component 44 moves with the subject's head when the subject leans her ear towards her shoulder. A device 40 can include an inclinometer 48. Inclinometer 48 can be coupled to viewing tube 41 near a distal end 49. Inclinometer 48 can measure the degrees of rotation viewing tube 41 makes about horizontal viewing axis 46 while eye piece component 44 is held fixed relative to the subject's head.

Any appropriate method can be used to make a device provided herein. For example, common molding or casting techniques can be used to make a viewing tube, an eye piece component, and a calibration line. In some cases, an inclinometer can be commercially obtained.

Figure 5:
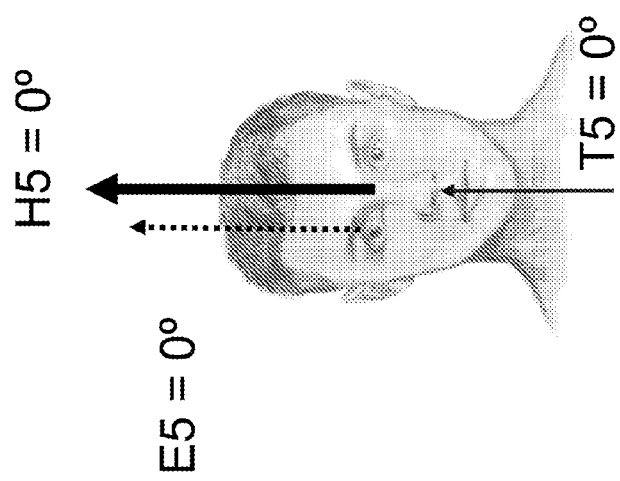
FIG. 5 is a diagram of a human's head showing three pertinent angles defined relative to vertical.

With reference to FIG. 5, there are three pertinent angles relative to vertical in defining OCR. For example, angle H5 represents the orientation or tilt of the head relative to gravitational zero. Angle H5 can be measured using the inclinometer of a device provided herein. Angle E5 defines the tilt angle of the eyes at head angle H5, and angle T5 represents the angle of the external target line (for example, a line projected onto a screen or wall). An additional angle, angle OCR can be defined as the difference between head angle H5 and eye angle E5. In FIG. 5, the head is in the neutral position, and the external target line is vertical, thus all of the pertinent angles are aligned at V Correspondingly, the difference between head angle H5 and eye angle E5 is 0°. This means that there is no OCR.

Figure 6:
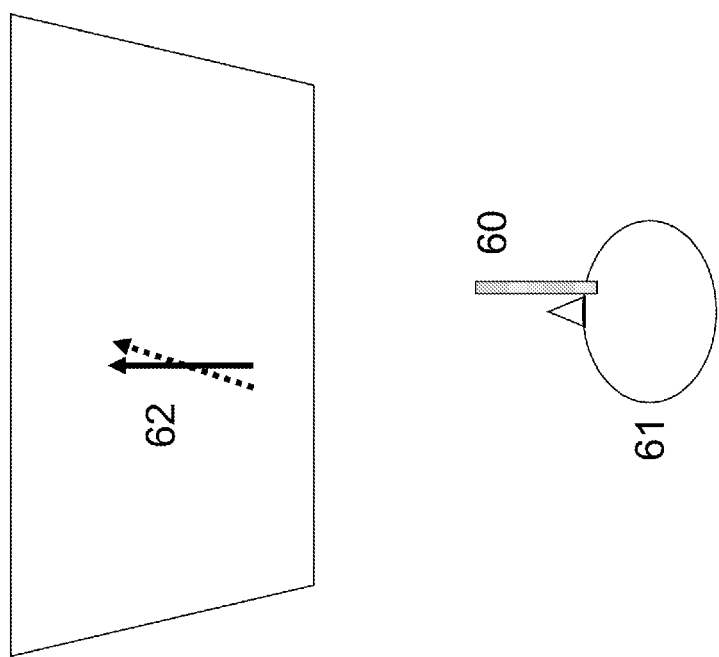
FIG. 6 is an example of a set-up configuration for measuring a baseline condition and OCR.

Any appropriate method can be used to measure the baseline condition with a device provided herein. For example, with reference to FIG. 6, a device 60 (such as a device provided herein) can be brought to one eye, while the opposite eye is covered such that subject 61 can only see out of a viewing tube. Subject 61 can then be directed to look at an external target line 62, for example, a target line 62 projected onto a screen or wall at a distance of about 1 to 6 meters (e.g., about 1, 2, 3, 4, 5, or 6 meters) from the subject. External target line 62 and the head of subject 61 are aligned to vertical. In this position, the calibration line within the viewing tube is manually adjusted to be parallel to external target line 62. For example, when device 10 has one inclinometer 17 as shown in FIG. 1, device 10 can be manually rotated until calibration line 13 within a viewing tube is parallel to the external target line. In some cases, as in FIG. 4, when the device has two inclinometers 47 and 48 or one inclinometer 48, viewing tube 41 can be manually rotated about viewing axis 46, while eye piece 44 is held fixed, until calibration line 43 is parallel to the external target line. When calibration line 43 is parallel to the external target line, measurements from inclinometers 47 and 48 can be taken as the baseline condition.

Figure 7:
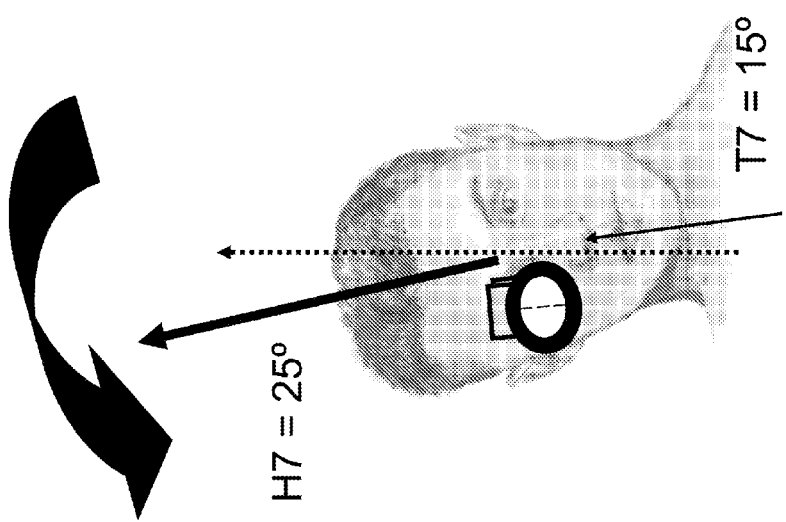
FIG. 7 is a diagram of a human's head showing the use of one example of a device provided herein to quantify OCR.

Once the baseline condition has been measured, OCR can be measured using a device provided herein. For example, an external target line can be tilted at an angle of 20° or less. With the device fixed relative to the subject's head, the subject can then be instructed to tilt their head such that the calibration line of the device is perceived to be parallel to the tilted external target line. Because the eye counter rolls, the head tilt will be greater than the tilt of the target line. This difference between head tilt and target tilt is proportional to the amount of OCR. It follows that by measuring the amount of head tilt required to perceptually match the tilt of a visual target, one can indirectly measure the effect of OCR. With the subject's head tilted, the inclinometer can be read to measure the exact amount of head tilt. With reference to FIG. 7, the external target line is tilted such that angle T7 is 15°. The subject perceives that the calibration line inside the viewing tube is parallel to the tilted external target line when the head is tilted at angle H7 (25°). The difference between head angle H7 and external target line angle T7 is 10°, and therefore OCR is 10°.

Figure 8:
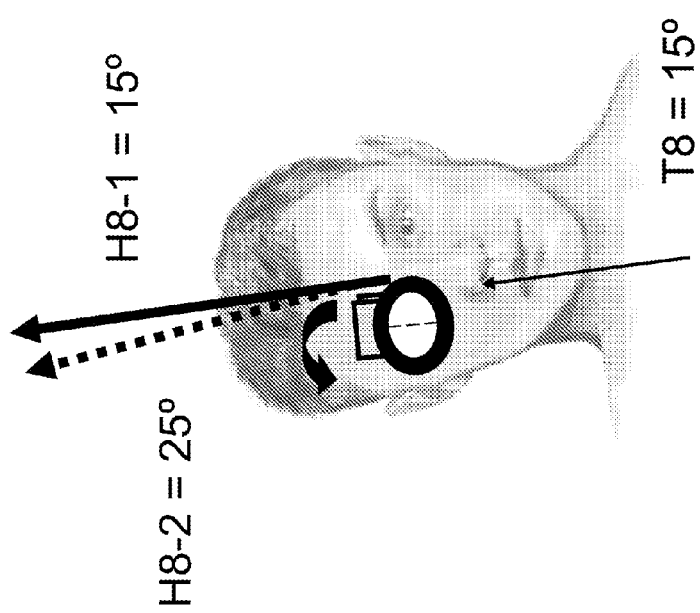
FIG. 8 is a diagram of a human's head showing the use of one example of a device provided herein to quantify OCR.

In some cases, OCR can be measured by manually turning the viewing tube about the viewing axis. For example, with a device to quantify OCR fixed relative to the subject's head, the subject's head can be manually tilted to the same angle as the external target line. The angle of head tilt can be measured with the inclinometer attached to the eye piece component. The subject will not perceive the calibration line inside the viewing tube and the tilted external target line as parallel due to OCR. The subject can then be instructed to turn manually the viewing tube about the viewing axis such that the calibration line inside the viewing tube is perceived to be parallel to the tilted external target line. The amount of OCR can be quantified by the inclinometer attached to the viewing tube as the amount of adjustment needed to align the calibration line inside the viewing tube and the tilted external target line. With reference to FIG. 8, the external target line is tilted such that angle T8 is 15°. The subject's head is manually tilted such that angle H8-1 is 15° and equals angle T8. The subject adjusts the viewing tube about the viewing axis until the calibration line inside the viewing tube is perceived to be parallel to the tilted external target line at angle H8-2 (25°). The difference between head angle H8-1 and H8-2 is 10°, and therefore OCR is 10°.

EXAMPLES

Example 1

Quantifying OCR

Figure 9:
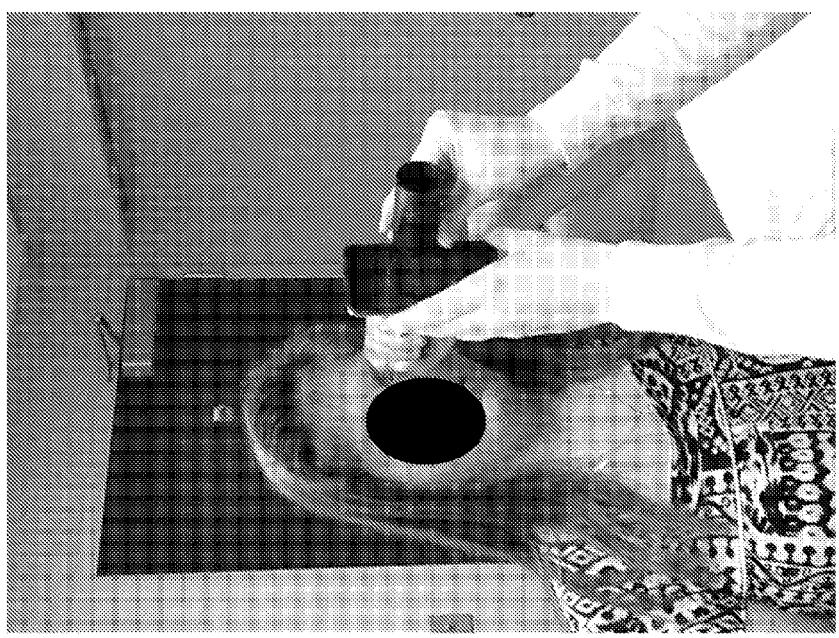
FIG. 9 is a photograph of a human and clinician using one example of a device provided herein to quantify OCR.

OCR was quantified in two subjects using a device having a viewing tube with a length of 20 and diameter of approximately 3 cm. An I-Pod with an inclinometer application was mounted onto the distal end of the viewing tube such that the edge of the I-Pod created the calibration line within the viewing tube (FIG. 9). The external target line was tilted at angles of −11° and 11°. With the device fixed relative to the subject's head, the head tilt required to perceive the calibration line inside the viewing tube as parallel to the tilted external target line was measured. Measurements were taken every 10 seconds for a total of 40 seconds.

Figure 10:
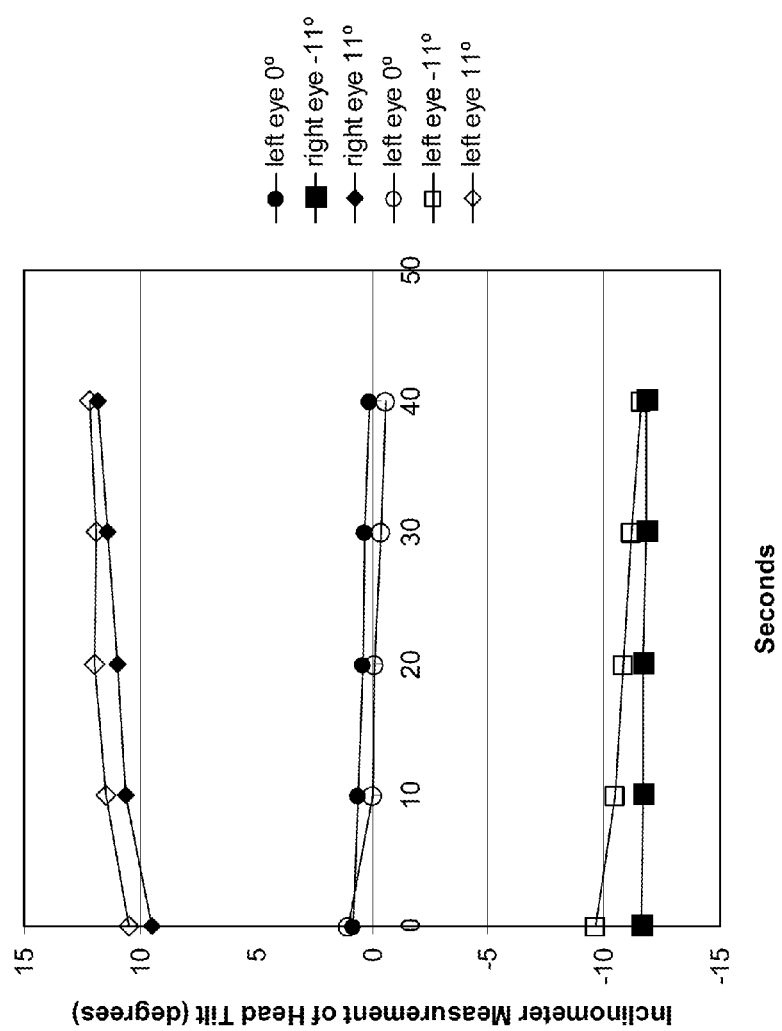
FIG. 10 is a scatter graph plotting head tilt measurements taken from subject 1 using an inclinometer of a device provided herein to quantify OCR with an external target line at 11°, 0°, and −11°. Readings were taken every 10 seconds for 40 seconds.
Figure 11:
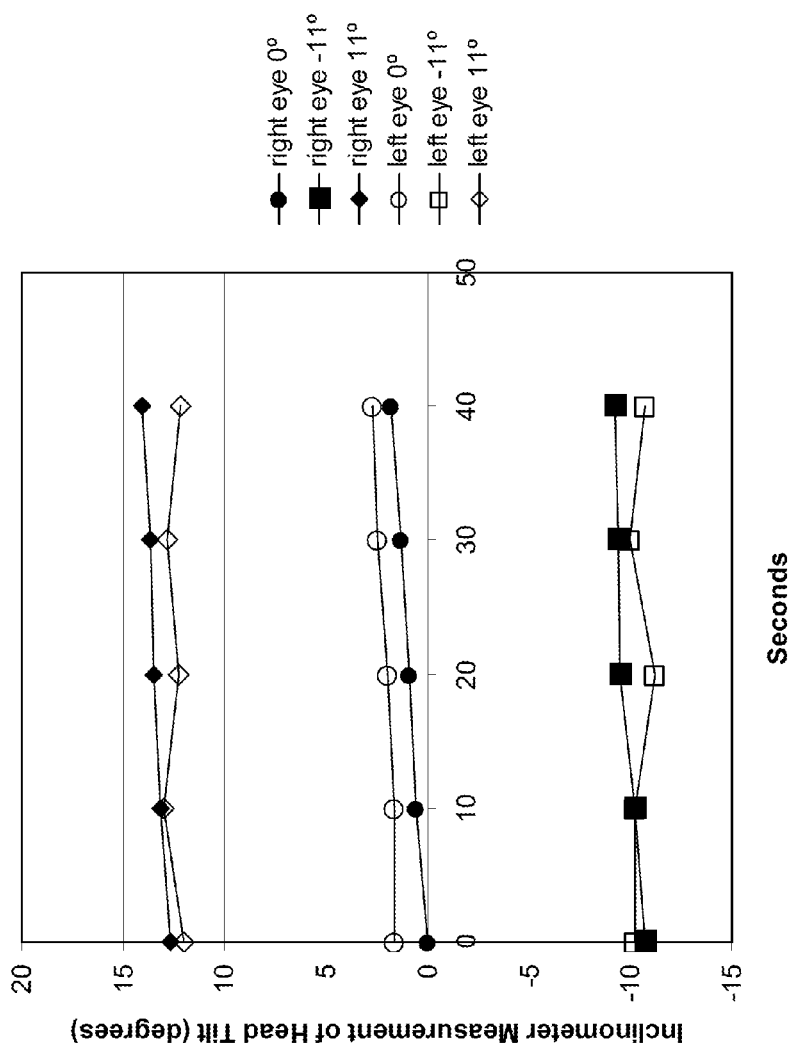
FIG. 11 is a scatter graph plotting head tilt measurements taken from subject 2 using an inclinometer of a device provided herein to quantify OCR with an external target line at 11°, 0°, and −11°. Readings were taken every 10 seconds for 40 seconds.

The measurements showed change over time, which is consistent with eye recordings (FIGS. 10 and 11). The average measured head tilt was 11.75° and −11.27° degrees, each greater than the respective target tilts of 11° and −11°. The measured OCR values were 0.75° and 0.27° and are consistent with normal OCR values (recognizing that the estimated OCR will vary with viewing distance.) Differences were noted between right and left eyes. This likely reflects subtle differences in eye muscle tone (phorea), which were substantial in one of the subjects used to collect these data.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for quantifying ocular counter roll, wherein said device comprises:
   (a) a viewing tube configured to have a hollow inner lumen;
   (b) a calibration line configured to be fixed with respect to said viewing tube;
   (c) an eye piece component configured to have a hollow inner lumen wherein said eye piece component allows a clear viewing path through said viewing tube; and
   (d) an inclinometer.

2. The device of claim 1, wherein said device is mechanically fixed to viewing goggles, glasses, or a handle.

3. The device of claim 1, wherein said viewing tube is configured to fit over an end of said eye piece component.

4. The device of claim 1, wherein said device comprises two inclinometers.

5. A method for quantifying ocular counter roll using a device comprising a viewing tube, a calibration line configured to be fixed with respect to said viewing tube, an eye piece component configured to allow a clear viewing path through said viewing tube, and an inclinometer to view an external target line placed within about 1 to 6 meters of the subject, wherein said method comprises:
   (a) obtaining a baseline measurement from said inclinometer when a subject perceives said calibration line and said external target line are parallel;
   (b) adjusting the angle of said external target line by 20° or less;
   (c) measuring the angle of said subject's head tilt with said inclinometer when said subject perceives said calibration line and said external target line are parallel; and
   (d) quantifying ocular counter roll as the difference between the angle of said external target line and the measured angle of said subject's head tilt.

6. The method of claim 5, wherein said device comprises two inclinometers.

7. A method for quantifying ocular counter roll using a device comprising a viewing tube, a calibration line configured to be fixed with respect to said viewing tube, an eye piece component configured to allow a clear viewing path through said viewing tube, and an inclinometer to view an external target line placed within about 1 to 6 meters of the subject, wherein said method comprises:
   (a) a human subject looking through said eye piece component and said viewing tube to visualize said calibration line and said external target line;
   (b) said subject, optionally, calibrating said device by manually rotating said viewing tube about the viewing axis until said calibration line and said external target line are parallel;
   (c) said subject tilting said subject's head with said device held fixed in relation to said subject's head until said subject perceives said calibration line and said external target line are parallel after the angle of said external target line is tilted by 20° or less; and
   (d) quantifying ocular counter roll as the difference between said subject's head tilt and external target line tilt.

8. The method of claim 7, wherein said subject's vision from the opposite eye is precluded.

9. A method for quantifying ocular counter roll using a device comprising a viewing tube, a calibration line configured to be fixed with respect to said viewing tube, an eye piece component configured to allow a clear viewing path through said viewing tube, and an inclinometer to view an external target line placed within about 1 to 6 meters of the subject, wherein said method comprises:
- (a) obtaining a baseline measurement from said inclinometer attached to said eyepiece component when a subject perceives said calibration line and said external target line are parallel;
- (b) adjusting the angle of said external target line by 20° or less;
- (c) manually tilting said subject's head to the same angle as said external target line with said device held fixed in relation to said subject's head, measuring head tilt angle with said inclinometer attached to said eye piece;
- (d) measuring the angle of said subject's head tilt adjustment with said inclinometer attached to said viewing tube after said subject perceives said calibration line and said external target line are parallel; and
- (e) quantifying ocular counter roll as the amount of said subject's head tilt adjustment.

10. The method of claim 9, wherein said subject's vision from the opposite eye is precluded.

11. The method of claim 9, wherein said device is mechanically fixed to viewing goggles, glasses, or a handle.

12. The method of claim 9, wherein said eye piece component is configured to fit over an end of said viewing tube.

13. The method of claim 9, wherein said viewing tube is configured to fit over an end of said eye piece component.

14. The method of claim 9, wherein said device comprises two inclinometers.

15. A method for quantifying ocular counter roll using a device comprising a viewing tube, a calibration line configured to be fixed with respect to said viewing tube, an eye piece component configured to allow a clear viewing path through said viewing tube, and an inclinometer to view an external target line placed within about 1 to 6 meters of the subject, wherein said method comprises:
- (a) a human subject looking through said eye piece component and said viewing tube to visualize said calibration line and said external target line;
- (b) said subject calibrating said viewing tube, if needed, by manually rotating said viewing tube about the viewing axis while fixing said eye piece component relative to the viewer's head until said calibration line and said external target line are parallel;
- (c) said subject allowing their head to be adjusted to the same angle of 20° or less as said external target line with said device held fixed in relation to said subject's head;
- (d) said subject adjusting their head tilt angle with said viewing tube held fixed in relation to said subject's head until said subject perceives said calibration line and said external target line are parallel; and
- (e) quantifying ocular counter roll as the amount of said subject's head tilt adjustment.

16. The method of claim 15, wherein said subject's vision from the opposite eye is precluded.

17. The method of claim 15, wherein said eye piece component is configured to fit over an end of said viewing tube.

18. The method of claim 15, wherein said viewing tube is configured to fit over an end of said eye piece component.

19. The method of claim 15, wherein said device comprises two inclinometers.

20. A method for determining if a human subject has otolith damage, wherein said method comprises quantifying ocular counter roll of said subject according to the method of claim 5, comparing said ocular counter roll of said subject to ocular counter roll measurements of control subjects known not to have otolith damage, and diagnosing otolith damage if said ocular counter roll of said subject is smaller than or larger than a counter roll of control subjects known not to have otolith damage.

* * * * *

UNITED STATES PATENT AND TRADEMARK OFFICE
CERTIFICATE OF CORRECTION

PATENT NO. : 9,332,904 B2  Page 1 of 1
APPLICATION NO. : 14/122599
DATED : May 10, 2016
INVENTOR(S) : David A. Zapala It is certified that error appears in the above-identified patent and that said Letters Patent is hereby corrected as shown below:

In the claims
Column 12, line 32 (approx.), please delete "otholith" and insert -- otolith --, therefor.

Signed and Sealed this
Twelfth Day of July, 2016

Michelle K. Lee
*Director of the United States Patent and Trademark Office*